(12) United States Patent
Anifowose et al.

(10) Patent No.: US 12,618,324 B2
(45) **Date of Patent: *May 5, 2026**

(54) PREDICTING FORMATION PORE PRESSURE IN REAL TIME BASED ON MUD GAS DATA

(71) Applicant: SAUDI ARABIAN OIL COMPANY, Dhahran (SA)

(72) Inventors: Fatai A. Anifowose, Al-Khobar (SA); Mokhles M. Mezghani, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 1028 days.

This patent is subject to a terminal disclaimer.

(21) Appl. No.: 17/644,869

(22) Filed: Dec. 17, 2021

(65) Prior Publication Data

US 2023/0193753 A1     Jun. 22, 2023

(51) Int. Cl.
E21B 44/00          (2006.01)
E21B 21/06          (2006.01)
(Continued)

(52) U.S. Cl.
CPC .......... E21B 49/005 (2013.01); E21B 21/067 (2013.01); E21B 44/00 (2013.01);
(Continued)

(58) Field of Classification Search
None
See application file for complete search history.

(56) References Cited

U.S. PATENT DOCUMENTS

2011/0088895 A1    4/2011   Pop et al.
2014/0116776 A1    5/2014   Marx et al.
(Continued)

FOREIGN PATENT DOCUMENTS

WO       2016/134376 A1    8/2016

OTHER PUBLICATIONS

Zhang, Jincai, and Shangxian Yin. "Real-time pore pressure detection: indicators and improved methods." Geofluids 2017, No. 1 (2017): 3179617. (Year: 2017).*
(Continued)

*Primary Examiner* — Ryan F Pitaro
*Assistant Examiner* — Simeon P Drapeau
(74) *Attorney, Agent, or Firm* — Osha Bergman Watanabe & Burton LLP

(57)          ABSTRACT

A system for estimating a pore pressure value associated with a depth of a well subject to drilling operations may include a data repository for storing integrated mud gas and pore pressure data associated with one or more existing wells. The data repository may also store a machine learning (ML) engine. The system may also include one or more hardware processors configured to train a ML model using the ML engine and the integrated mud gas and pore pressure data, to estimate, during the drilling operations, the pore pressure value of a formation zone, at the depth of the well, using the trained ML model and mud gas data associated with a depth value that identifies the depth of the well subject to the drilling operations, and to update a drilling program for a production system based on the estimated pore pressure value.

17 Claims, 7 Drawing Sheets

(51) Int. Cl.

| | |
|---|---|
| *E21B 49/00* | (2006.01) |
| *G01N 33/00* | (2006.01) |
| *G01N 33/28* | (2006.01) |

(52) U.S. Cl.
CPC ..... *G01N 33/0027* (2013.01); *G01N 33/2823* (2013.01); *E21B 2200/20* (2020.05)

(56) References Cited

U.S. PATENT DOCUMENTS

| | | | | |
|---|---|---|---|---|
| 2015/0267527 | A1* | 9/2015 | Nguyen | G01V 3/20 |
| | | | | 702/12 |
| 2016/0097270 | A1* | 4/2016 | Pobedinski | G05B 17/02 |
| | | | | 700/275 |
| 2016/0222741 | A1 | 8/2016 | Lovorn et al. | |
| 2016/0341849 | A1* | 11/2016 | Shahri | E21B 49/006 |
| 2017/0260855 | A1 | 9/2017 | Yang et al. | |
| 2021/0332694 | A1* | 10/2021 | Wessling | E21B 21/08 |
| 2021/0348495 | A1* | 11/2021 | Anifowose | G06F 18/214 |
| 2021/0349001 | A1 | 11/2021 | Anifowose et al. | |

OTHER PUBLICATIONS

Abdelaal, Ahmed, Salaheldin Elkatatny, and Abdulazeez Abdulraheem. "Data-driven modeling approach for pore pressure gradient prediction while drilling from drilling parameters." ACS omega 6, No. 21 (2021): 13807-13816. (Year: 2021).*

Booncharoen, Pichita, Thananya Rinsiri, Pakawat Paiboon, Supaporn Karnbanjob, Sonchawan Ackagosol, Prateep Chaiwan, and Ouraiwan Sapsomboon. "Pore pressure estimation by using machine learning model." In International Petroleum Technology Conference, p. D012S045R069. IPTC, 2021. (Year: 2021).*

Farid ArabAmeri, Hamidreza Soleymani, Behzad Tokhmechi, "Enhanced velocity-based pore-pressure prediction using lithofacies clustering: a case study from a reservoir with complex lithology in Dezful Embayment, SW Iran", Journal of Geophysics and Engineering, vol. 16, Issue 1, Feb. 2019, pp. 146-158 (13 pages).

Abdulmalek Ahmed, Salaheldin Elkatatny, Abdulwahab Ali, Mohamed Mahmoud and Abdulazeez Abdulraheem, "New Model for Pore Pressure Prediction While Drilling Using Artificial Neural Networks", Arabian Journal for Science and Engineering, vol. 44, pp. 6079-6088, 2019 (10 pages).

P. S. Hutomo, M. S. Rosid and M. W. Haidar, "Pore Pressure Prediction Using Eaton and Neural Network Method in Carbonate Field "X" Based on Seismic Data", IOP Conference Series: Materials Science and Engineering, vol. 546, Issue 3, 2019 (8 pages).

Farqad Hadi, Andreas Eckert, Faleh Almahdawi, "Real-Time Pore Pressure Prediction in Depleted Reservoirs Using Regression Analysis and Artificial Neural Networks", SPE-194857-MS, Paper presented at the SPE Middle East Oil and Gas Show and Conference, Manama, Bahrain, Mar. 2019 (14 pages).

Dutta, N., Bachrach, R., & Mukerji, T. (2021). Geopressure Detection and Prediction in Real Time. In Quantitative Analysis of Geopressure for Geoscientists and Engineers (pp. 348-367). Cambridge: Cambridge University Press (20 pages).

Morteza Azadpour, Navid Shad Manaman, Ali Kadkhodaie-Ilkhchi, Mohammad-Reza Sedghipour, "Pore pressure prediction and modeling using well-logging data in one of the gas fields in south of Iran", Journal of Petroleum Science and Engineering, vol. 128, 2015, pp. 15-23 (9 pages).

Libin Liu, Guoqiang Shen, Zhentao Wang, Hongwei Yang, Hongwei Han, Yuanfeng Cheng, "Abnormal formation velocities and applications to pore pressure prediction", Journal of Applied Geophysics 153 (2018) pp. 1-6 (6 pages).

Yukun Liu, Zhiliang He, Sheng He, Dianwei Zhang, Tianyi Li, Xiaolong Wang, "A new quantitative model and application for overpressure prediction in carbonate formation", Journal of Petroleum Science and Engineering, vol. 198, Mar. 2021 (15 pages).

Mohammad Farsi, Nima Mohamadian, Hamzeh Ghorbani, David A. Wood, Shadfar Davoodi, Jamshid Moghadasi and Mehdi Ahmadi Alvar, "Predicting Formation Pore-Pressure from Well-Log Data with Hybrid Machine-Learning Optimization Algorithms". Natural Resources Research (2021) (27 pages).

Jincai Zhang and Shangzian Yin, "Real-Time Pore Pressure Detection: Indicators and Improved Methods", Wiley Hindawi, Geofluids, vol. 2017 (13 pages).

Ahmed Abdelaal, Salaheldin Elkatatny, and Abdulazeez Abdulraheem, "Data-Driven Modeling Approach for Pore Pressure Gradient Prediction while Drilling from Drilling Parameters", ACS Omega, vol. 6, Issue 21, pp. 13807-13816, 2021 (10 pages).

Abdulmalek Ahmed S, Salaheldin Elkatatny, Abdulwahab Z Ali, Abdulazeez Abdulraheem, and Mohamed Mahmoud, King Fahd University of Petroleum & Minerals, "Artificial Neural Network ANN Approach to Predict Fracture Pressure", Society of Petroleum Engineers, SPE-194852-MS, Paper presented at the SPE Middle East Oil and Gas Show and Conference, Manama, Bahrain, Mar. 2019 (9 pages).

Office Action issued by Saudi Arabian Patent Office for corresponding Saudi Patent Application No. 122440873, mailed Mar. 4, 2025 (20 pages).

\* cited by examiner

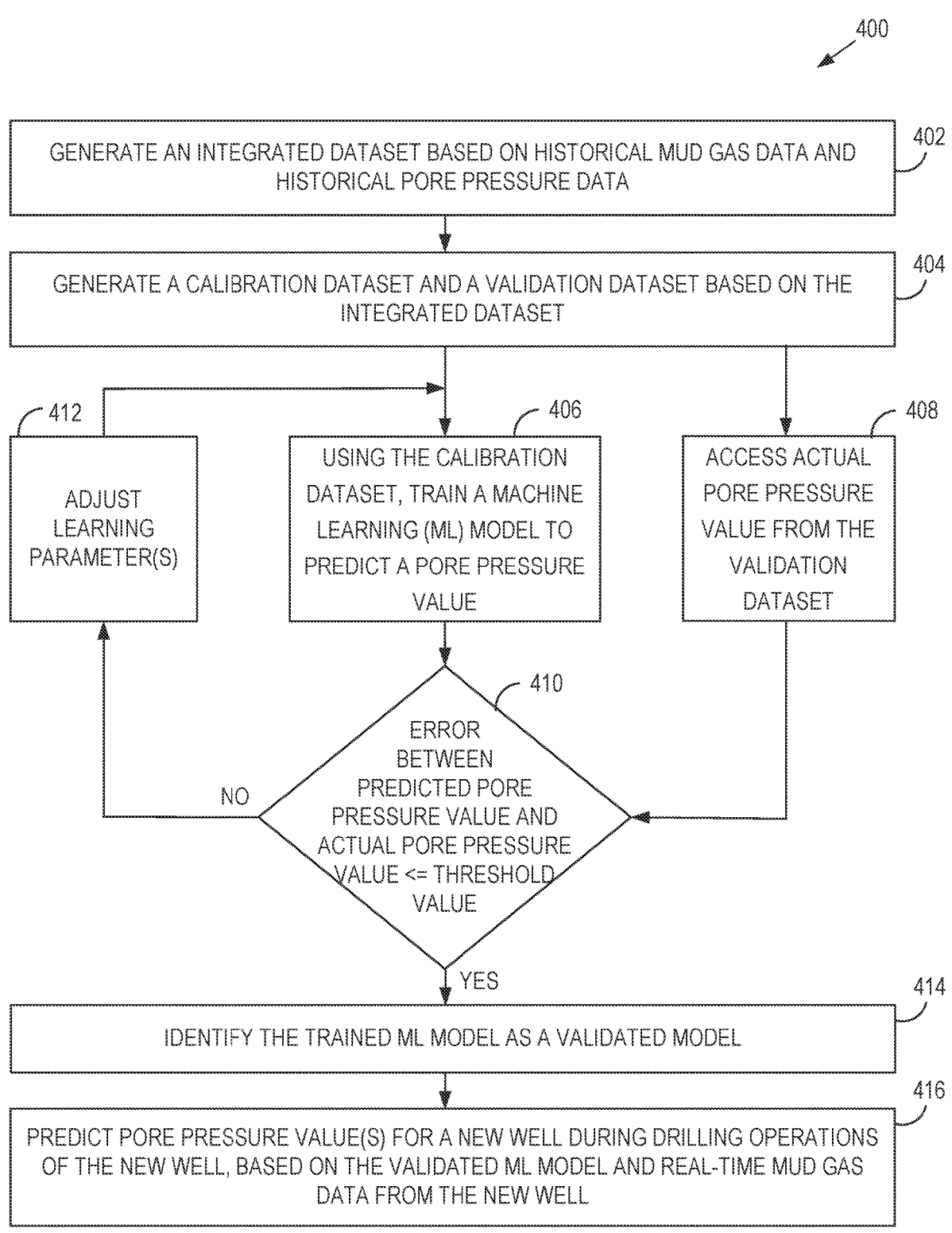

400

402
GENERATE AN INTEGRATED DATASET BASED ON HISTORICAL MUD GAS DATA AND HISTORICAL PORE PRESSURE DATA

404
GENERATE A CALIBRATION DATASET AND A VALIDATION DATASET BASED ON THE INTEGRATED DATASET

412
ADJUST LEARNING PARAMETER(S)

406
USING THE CALIBRATION DATASET, TRAIN A MACHINE LEARNING (ML) MODEL TO PREDICT A PORE PRESSURE VALUE

408
ACCESS ACTUAL PORE PRESSURE VALUE FROM THE VALIDATION DATASET

410
ERROR BETWEEN PREDICTED PORE PRESSURE VALUE AND ACTUAL PORE PRESSURE VALUE <= THRESHOLD VALUE

NO

YES

414
IDENTIFY THE TRAINED ML MODEL AS A VALIDATED MODEL

416
PREDICT PORE PRESSURE VALUE(S) FOR A NEW WELL DURING DRILLING OPERATIONS OF THE NEW WELL, BASED ON THE VALIDATED ML MODEL AND REAL-TIME MUD GAS DATA FROM THE NEW WELL

FIG. 4

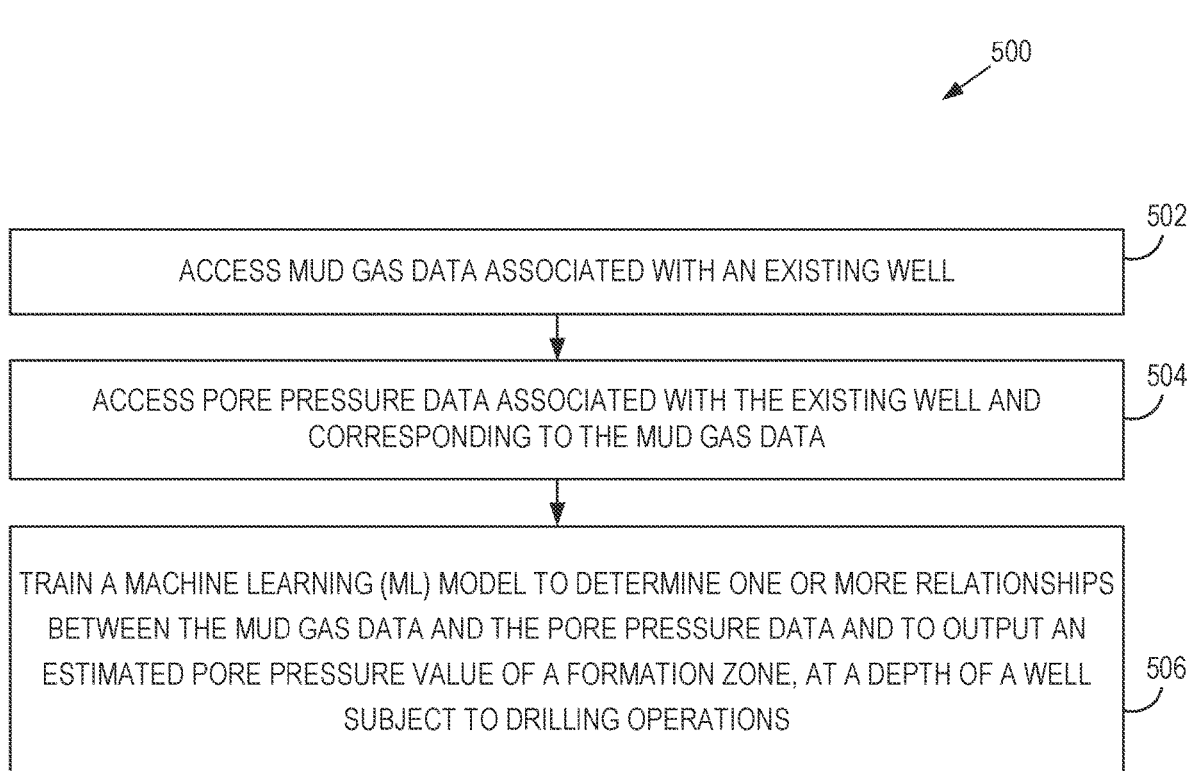

500

502

ACCESS MUD GAS DATA ASSOCIATED WITH AN EXISTING WELL

504

ACCESS PORE PRESSURE DATA ASSOCIATED WITH THE EXISTING WELL AND
CORRESPONDING TO THE MUD GAS DATA

TRAIN A MACHINE LEARNING (ML) MODEL TO DETERMINE ONE OR MORE RELATIONSHIPS
BETWEEN THE MUD GAS DATA AND THE PORE PRESSURE DATA AND TO OUTPUT AN
ESTIMATED PORE PRESSURE VALUE OF A FORMATION ZONE, AT A DEPTH OF A WELL
SUBJECT TO DRILLING OPERATIONS

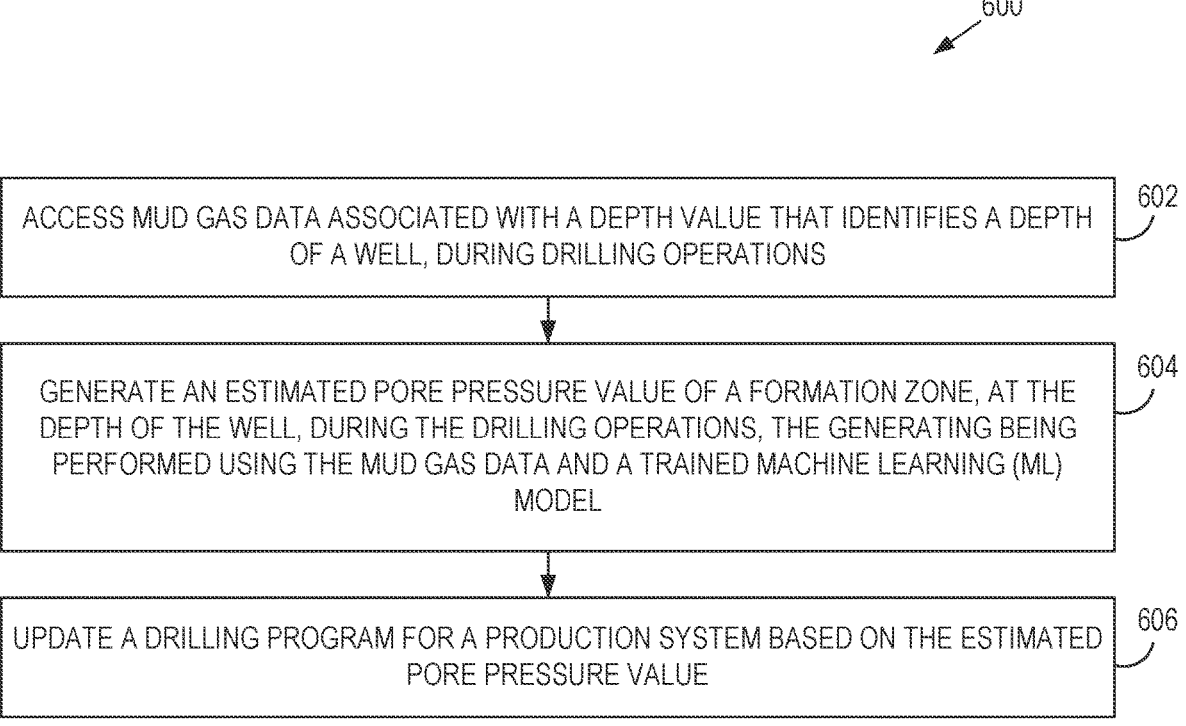

600

ACCESS MUD GAS DATA ASSOCIATED WITH A DEPTH VALUE THAT IDENTIFIES A DEPTH OF A WELL, DURING DRILLING OPERATIONS     602

GENERATE AN ESTIMATED PORE PRESSURE VALUE OF A FORMATION ZONE, AT THE DEPTH OF THE WELL, DURING THE DRILLING OPERATIONS, THE GENERATING BEING PERFORMED USING THE MUD GAS DATA AND A TRAINED MACHINE LEARNING (ML) MODEL     604

UPDATE A DRILLING PROGRAM FOR A PRODUCTION SYSTEM BASED ON THE ESTIMATED PORE PRESSURE VALUE     606

FIG. 6

PREDICTING FORMATION PORE PRESSURE IN REAL TIME BASED ON MUD GAS DATA

BACKGROUND

Conventionally, pore pressure analyses include three aspects: pre-drill pore pressure prediction, pore pressure prediction while drilling, and post-well pore pressure analysis. The pre-drill pore pressure is predicted using seismic interval velocity data in the planned well location, as well as geological, well logging, and drilling data in offset wells. The pore pressure prediction while drilling mainly uses logging while drilling (LWD) data, measurement while drilling (MWD) data, drilling parameters, and mud lithology data for analyses. Pore pressure may be calculated based on overburden and effective stresses. Overburden stress may be determined from bulk density logs, while effective stress is correlated to well log data, such as resistivity, sonic travel time or velocity, bulk density, and drilling parameters (e.g., D exponent). The post-well analysis may include analysis of pore pressures in the drilled wells using available data to build a pore pressure model. The pore pressure model may be used for pre-drill pore pressure predictions in future wells.

Pore pressure is commonly estimated from shale properties derived from well log data which include acoustic travel time or velocity and resistivity. Pore pressure has also been estimated using other wireline logs such as true vertical depth (TVD), unconfined compressive strength (UCS), gamma ray, neutron porosity (NPHI), and bulk density (RHOZ). Further, pore pressure has been estimated from combined drilling parameters and log data, such as weight on bit (WOB), rotary speed (RPM), rate of penetration (ROP), mud weight (MW), bulk density (RHOB), and porosity. In addition, pore pressure has been estimated from only seismic data or from rock elastic properties.

The conventional methods of estimating pore pressure may not have a high degree of accuracy because they may be based on empirical equations that assume linear relationships. Abnormal pore pressures may cause serious drilling incidents such as blowouts, kicks, fluid influx, pipe sticking, and lost circulation, and may greatly increase drilling nonproductive time. To avoid such incidents, pore pressure needs to be accurately estimated and closely monitored while drilling.

Accordingly, there is a need for a system that accurately predicts pore pressure ahead of coring, wireline logging, and formation testing activities, and without using seismic, surface drilling parameters, and wireline logs used in the current approaches.

SUMMARY

This summary is provided to introduce concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein relate to a system for estimating a pore pressure value associated with a depth of a well subject to drilling operations. The system includes a data repository for storing integrated mud gas and pore pressure data associated with one or more existing wells. The data repository also stores a machine learning (ML) engine. The system includes an access module configured to access the integrated mud gas and pore pressure data, to access the ML engine, and to access mud gas data associated with a depth value that identifies the depth of the well subject to the drilling operations. The system includes one or more hardware processors configured to train a ML model using the ML engine and the integrated mud gas and pore pressure data. The one or more hardware processors are also configured to estimate, during the drilling operations, the pore pressure value of a formation zone, at the depth of the well, using the trained ML model and the mud gas data associated with the depth value that identifies the depth of the well subject to the drilling operations. The one or more hardware processors are also configured to update a drilling program for a production system based on the estimated pore pressure value.

In general, in one aspect, embodiments disclosed herein relate to a method for estimating a pore pressure value associated with a depth of a well, during drilling operations. The method includes accessing mud gas data associated with a depth value that identifies the depth of the well subject to the drilling operations. The method includes generating an estimated pore pressure value of a formation zone, at the depth of the well, during the drilling operations, the generating being performed using one or more hardware processors, the mud gas data, and a trained machine learning (ML) model. The method includes updating a drilling program for a production system based on the estimated pore pressure value.

In general, in one aspect, embodiments disclosed herein relate to a method for training a machine learning (ML) model to estimate a pore pressure value associated with a depth of a well subject to drilling operations. The method includes accessing mud gas data associated with an existing well. The method includes accessing pore pressure data associated with the existing well and corresponding to the mud gas data. The method includes training, using one or more hardware processors, the ML model to determine one or more relationships between the mud gas data and the pore pressure data, and to output an estimated pore pressure value of a formation zone, at the depth of the well subject to the drilling operations, based on the one or more relationships between the mud gas data and the pore pressure data, and based on mud gas data associated with the well subject to the drilling operations.

Other aspects and advantages of the claimed subject matter will be apparent from the following description and the appended claims.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

FIG. 4 is a flow diagram that illustrates an algorithm for training a machine learning model to predict pore pressure values based on mud gas data, according to one or more example embodiments.

FIG. 5 is a flowchart illustrating operations of a system in performing a method for training the ML model to estimate a pore pressure value based on mud gas data, according to one or more example embodiments.

FIG. 6 is a flowchart illustrating operations of a system in performing a method for estimating a pore pressure value based on mud gas data during drilling operations, according to one or more example embodiments.

DETAILED DESCRIPTION

Figure 1:
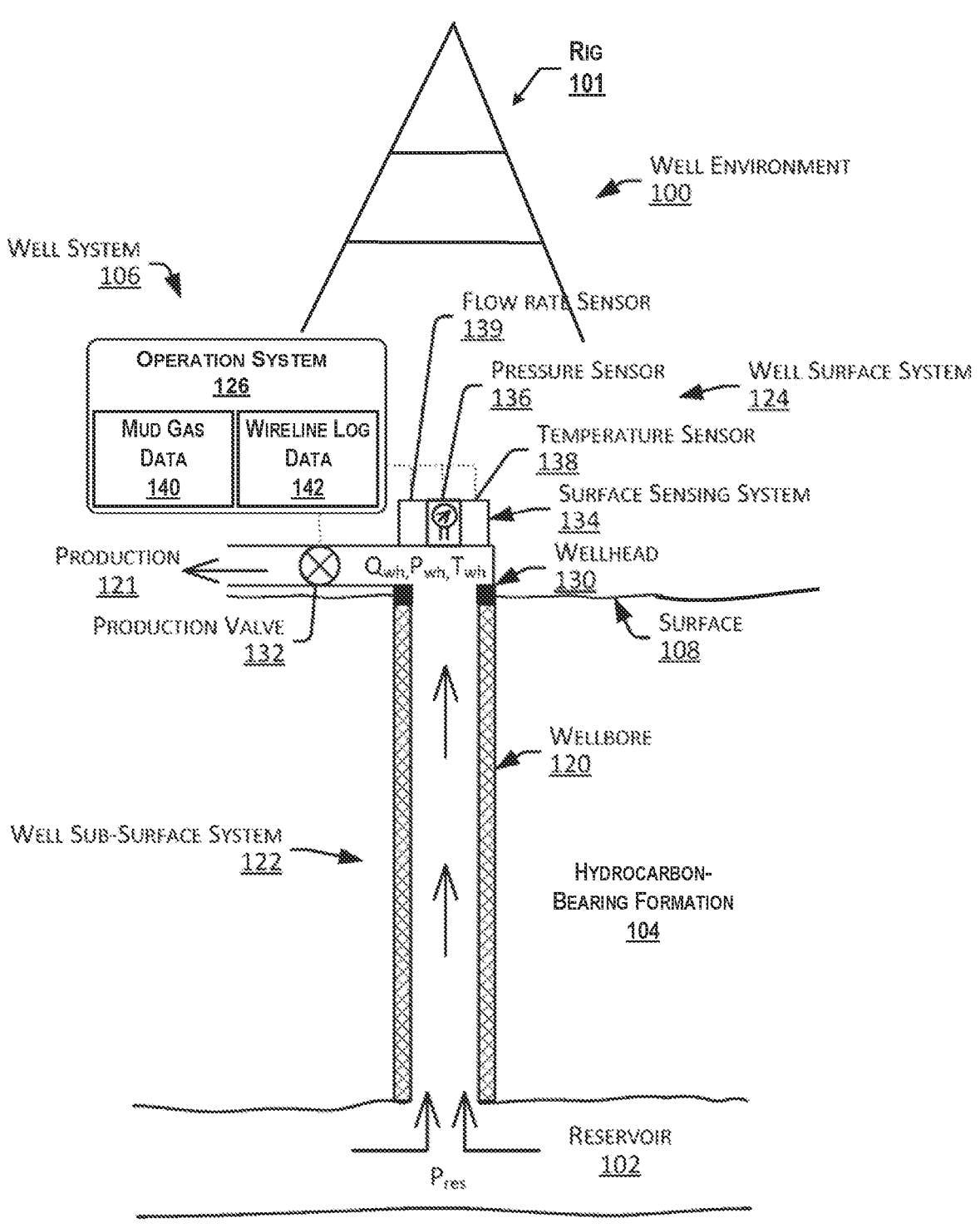
FIG. 1 illustrates a system, according to one or more example embodiments.

In example systems and methods for predicting formation pore pressure in real time based on mud gas data as discussed herein, components and functions are optional and may be combined or subdivided. Similarly, operations may be combined or subdivided, and their sequence may vary.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, or third) may be used as an adjective for an element (that is, any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

Formation pore pressure is the pressure exerted by the formation fluids on the walls of the rock pores in porous formations. Pore pressure estimation is an important component of a drilling plan. Pore pressure can exist in three forms: normal, underpressure, or overpressure. It is considered normal when the pore pressure is equal to the formation hydrostatic pressure. Underpressure is a situation when the pore pressure is lower than the hydrostatic pressure. In contrast, overpressure is a situation when the pore pressure is higher than the hydrostatic pressure. Both underpressure and overpressure conditions are considered abnormal. Abnormal pore pressures, especially overpressures, can greatly increase drilling non-productive time and cause serious drilling incidents such as blowouts, kicks, fluid influx, pipe sticking, and lost circulation. To avoid such incidents, pore pressure needs to be accurately estimated and closely monitored while drilling. Abnormal pressures can be caused by several mechanisms such as compaction disequilibrium, hydrocarbon generation and gas cracking, hydrothermal expansion, tectonic compression (lateral stress), mineral transformations such as illitization, osmosis, hydraulic head and hydrocarbon buoyancy. Knowing the pore pressure while drilling a well helps drillers to dynamically adjust the mud weight to stabilize the hydrostatic pressure, thereby preserving the integrity of the wellbore and ensuring an efficient drilling process.

According to one or more example embodiments, a system may predict formation pore pressure in a well undergoing drilling using a machine learning (ML) model and mud gas data generated based on the drilling fluid (hereinafter also "drilling mud" or "mud") returned from the wellbore and measured at the surface after separation of the gas components. ML models, such as artificial neural networks, a support vector machine, a decision tree, a random forest, a multivariate linear regression, etc., may be used to determine one or more relationships between mud gas data from a well and corresponding pore pressure data from the well. In some example embodiments, the ML model is configured and optimized with one or more hidden layers (depending on the volume and complexity of the training data), a sigmoid activation function in the hidden layer, a linear function in the summation layer, and training algorithms based on the Levenberg-Marquardt and Bayesian regulation backpropagation. Integrated datasets of mud gas data and pore pressure data from one or more existing wells may be used to train the ML model. Upon completing the training of the ML model, a mud gas value that is acquired in real time from a new well being drilled and that is associated with a depth of the new well may be used as input into the ML model to generate an estimated pore pressure value as an output corresponding to the mud gas value associated with the depth of the new well.

In some example embodiments, another integrated mud gas—pore pressure dataset generated from one or more other wells may be used to validate (and optimize) the performance of the ML model. The optimization process involves adjusting one or more learning parameters of the ML model, such as the learning rate, the number of neurons, the activation function, and weight coefficients, to their optimal values such that the error value between the predicted pore pressure value and an actual pore pressure value from the validation data subset is less than or equal to a predetermined threshold value. If the error value is less than or equal to the threshold value, the ML model is considered optimized and can receive real-time mud gas measurements from a new well to predict the pore pressure log profile for the new well, zone of interest, or zone of data coverage. If, however, the error value is greater than the threshold value, the system continues to adjust the learning parameters of the ML model.

In some example embodiments, the training (calibration) data subset is used to create a nonlinear mathematical relationship between the mud gas data and the pore pressure log. This may be done by multiplying each mud gas log by a certain weight factor determined by the outcome of the nonlinear mapping using an activation function. The weight factor (e.g., ranging from 0 to ±1) is obtained from the degree of nonlinear correlation or significance between the mud gas data and the pore pressure data. The weighting process determines the effect a gas measurement has on the model. A certain function, $f$, such as a sigmoid is used to transform the input space into a high-dimensional nonlinear space to match the valid ranges of the subsurface data including the mud gas measurements. A mathematical equation could be:

$$Y = f(a_1X_1 + a_2X_2 + \ldots + a_nX_n)$$

where Y is the target variable (pore pressure in this case), $a_1 \ldots a_n$ are the weighting factors, $X_1$-$X_n$ are examples of the input mud gas measurements, and $f$ is the activation function such as Gaussian or sigmoid.

A Gaussian function is in this form:

$$f(x) = e^{-x^2}$$

where x is each of the input wireline logs.

A sigmoid function is in this form:

$$f(x) = \frac{1}{1 + e^{-x}}$$

where x is each of the input wireline logs.

Parameters such as the number of layers and number of neurons in the hidden layer(s) are set to fit (also called tune) the nonlinear equation to the calibration data. The input part of the validation dataset (i.e., the mud gas measurements) is passed to the ML model while keeping the target variable hidden. The ML model is used to estimate the corresponding target (i.e., the pore pressure values) to the input gas measurements. The estimated target values are then compared to the actual target values kept hidden from the model. If the residual (e.g., the difference between an estimated target value and an actual target value) is equal to or greater than a certain threshold value, one or more parameters are adjusted and the validation process is repeated. The validation cycle continues until the residual comes within the defined threshold value. When the residual is determined to be less than the threshold value, the ML model may be identified as a "validated" trained ML model ready for real-time prediction of pore pressure for a new well while drilling is performed.

The prediction process involves porting the mud gas measurements for a new well being drilled to the trained ML model (i.e., the calibrated mathematical equation) to estimate and generate a new pore pressure as a log. The validated ML model takes in the mud gas measurements as input and generates from it a log of pore pressure in the same depth interval as the mud gas measurements.

In certain example embodiments, the ML model is re-calibrated based on the data received from the new well undergoing the drilling operations. When new or additional data (i.e., mud gas measurements and their corresponding pore pressure estimations from newly drilled and analyzed wells) is available, they may be added to the existing calibration database. With the updated calibrated database, the same set of tuning parameters may no longer be sufficient to fit the ML model to the newly updated data. Hence, new sets of the tuning parameters may be derived to establish a good fit between the updated mud gas measurements and the new set of pore pressure estimations.

According to some example embodiments, a system for estimating a pore pressure value associated with a depth of a well subject to drilling operations, comprises a data repository for storing integrated mud gas and pore pressure data associated with one or more existing wells, and a machine learning (ML) engine. The system further comprises an access module configured to access the integrated mud gas and pore pressure data, to access the ML engine, and to access mud gas data associated with a depth value that identifies the depth of the well subject to the drilling operations. The system further comprises one or more hardware processors configured to train an ML model using the ML engine and the integrated mud gas and pore pressure data. The one or more hardware processors are further configured to estimate, during the drilling operations, the pore pressure value of a formation zone, at the depth of the well, using the trained ML model and the mud gas data associated with the depth value that identifies the depth of the well subject to the drilling operations. The one or more hardware processors are further configured to update a drilling program for a production system based on the estimated pore pressure value.

The system for predicting formation pore pressure based on mud gas data provides a number of benefits when compared to conventional methods of determining formation pore pressure. The system predicts formation pore pressure in real time from mud gas data obtained based on mud returned to the surface during the drilling operations of a new well, before coring, wireline logging, and formation testing activities are performed. Further, the system utilizes the mud gas data acquired directly from the wellbore without being affected by human bias. The use of machine learning to establish nonlinear relationships between the mud gas data and the pore pressure data facilitates a more accurate analysis of the data than the conventional approaches that are based on empirical equations that assume linear relationships.

Additional advantages of the system predicting pore pressure as a log in real time are: adjusting the weight on bit dynamically to prevent various drilling issues such as blow-out, gas kicks, stuck pipe, fluid influx, and lost circulation, thereby increasing safety and increasing drilling efficiency; dynamically adjusting drilling mud properties such as density and rheology, thereby increasing the rate of penetration; providing valuable information for well control and geo-steering; dynamically determining optimal casing points while drilling; dynamically detecting zones of poor quality LWD measurements; and dynamically detecting zones of hydrocarbon existence.

FIG. 1 shows a schematic diagram of a system, in accordance with one or more embodiments. FIG. 1 illustrates a well environment 100 that includes a hydrocarbon reservoir ("reservoir") 102 located in a subsurface hydrocarbon-bearing formation ("formation") 104 and a well system 106. The hydrocarbon-bearing formation 104 may include a porous or fractured rock formation that resides underground, beneath the Earth's surface ("surface") 108. In the case of the well system 106 being a hydrocarbon well, the reservoir 102 may include a portion of the hydrocarbon-bearing formation 104. The hydrocarbon-bearing formation 104 and the reservoir 102 may include different layers of rock having varying characteristics, such as varying degrees of permeability, porosity, capillary pressure, and resistivity. In the case of the well system 106 being operated as a production well, the well system 106 may facilitate the extraction (or "production") of hydrocarbons from the reservoir 102.

In some embodiments disclosed herein, the well system 106 includes a rig 101, a wellbore 120, a well sub-surface system 122, a well surface system 124, and an operation system 126. The operation system 126 may control various operations of the well system 106, such as well production operations, well completion operations, well maintenance operations, and reservoir monitoring, assessment, and development operations. In some embodiments, the operation system 126 includes a computer system that is the same as or similar to computing system 700 described below in FIG. 7, and the accompanying description.

The rig 101 is the machine used to drill a borehole to form the wellbore 120. Major components of the rig 101 include the mud tanks, the mud pumps, the derrick or mast, the drawworks, the rotary table or topdrive, the drillstring, the power generation equipment, and auxiliary equipment.

The wellbore 120 includes a bored hole (i.e., borehole) that extends from the surface 108 into a target zone of the hydrocarbon-bearing formation 104, such as the reservoir 102. An upper end of the wellbore 120, terminating at or near the surface 108, may be referred to as the "up-hole" end of the wellbore 120, and a lower end of the wellbore, terminating in the hydrocarbon-bearing formation 104, may be referred to as the "downhole" end of the wellbore 120. The wellbore 120 may facilitate the circulation of drilling fluids during drilling operations, the flow of hydrocarbon production ("production") 121 (e.g., oil, gas, or both) from the reservoir 102 to the surface 108 during production operations, the injection of substances (e.g., water) into the hydrocarbon-bearing formation 104 or the reservoir 102 during injection operations, or the communication of monitoring devices (e.g., logging tools) into the hydrocarbon-bearing formation 104 or the reservoir 102 during monitoring operations (e.g., during in situ logging operations).

In some embodiments, during operation of the well system 106, starting from the rig platform, mud is pumped down the wellbore 120 with high pressure to the formation 104 through the drill pipe. The mud may serve the purposes of lubricating the drill bit, neutralizing the formation pressure, and conveying the drill cuttings and other debris from the wellbore 120 to the surface 108. The returned mud is collected at the surface 108 in the separator tank where the mud is degassed using an agitator. The degassed mud flows over a shale shaker, where the cuttings and other debris are separated from the filtered mud. The filtered mud is collected in the mud tank to be pumped back into the wellbore 120. The gas mixture that is extracted from the mud is analyzed using a gas analysis tool. The gas analysis tool may include a gas sampler, a chromatograph, and a spectrometer to separate and measure the gas components included in the gas mixture. The gas analysis may identify the gas components as light or heavy, as well as the organic or inorganic. The results of the gas analysis may be stored as mud gas data 140 in a data repository. In some embodiments, the mud gas data 140 is recorded in real-time (or near real time), and is available for review or use within seconds, minutes, or hours of the gas analysis. In such an embodiment, the mud gas data 140 may be referred to as "real-time" mud gas data 140. Real-time mud gas data 140 may enable an operator of the well system 106 to assess a relatively current state of the well system 106, and make real-time decisions regarding development or management of the well system 106 and the reservoir 102, such as on-demand adjustments in regulation of production flow from the well. In some instances, the real-time decisions are performed automatically.

According to some example embodiments, the operation system 126 collects and records wireline log data 142 for the well system 106. The collecting of the wireline log data 142 may include continuous measurement of formation properties with electrically powered instruments to determine the properties of formation rock. The collected measurements may include electrical properties (e.g., resistivity and conductivity at various frequencies), sonic properties, active and passive nuclear measurements, dimensional measurements of the wellbore, formation fluid sampling, and formation pressure (also "pore pressure") measurement. In some instances, to collect the wireline measurements, a logging tool is lowered into the open wellbore on a multiple conductor, contra-helically armored wireline cable. Once a tool string of the logging tool has reached the bottom of the interval of interest, measurements are taken on the way out of the wellbore. In certain example embodiments, the wireline logging tools include one or more sensors inserted in the wellbore 120 via a cable to measure certain rock properties at different depth points (e.g., every half a foot).

In various example embodiments, the operation system 126 trains a ML model to predict a pore pressure value at a certain depth of a well based on real-time or near real-time mud gas data 140 acquired during drilling operations of the well. The training of the ML model may be based on historical mud gas data and historical pore pressure data that corresponds to the historical mud gas data collected from existing wells.

In some embodiments, the well sub-surface system 122 includes casing installed in the wellbore 120. For example, the wellbore 120 may have a cased portion and an uncased (or "open-hole") portion. The cased portion may include a portion of the wellbore having casing (e.g., casing pipe and casing cement) disposed therein. The uncased portion may include a portion of the wellbore not having casing disposed therein. In some embodiments, the casing includes an annular casing that lines the wall of the wellbore 120 to define a central passage that provides a conduit for the transport of tools and substances through the wellbore 120. For example, the central passage may provide a conduit for lowering logging tools into the wellbore 120, a conduit for the flow of production 121 (e.g., oil and gas) from the reservoir 102 to the surface 108, or a conduit for the flow of injection substances (e.g., water) from the surface 108 into the hydrocarbon-bearing formation 104. In some embodiments, the well sub-surface system 122 includes production tubing installed in the wellbore 120. The production tubing may provide a conduit for the transport of tools and substances through the wellbore 120. The production tubing may, for example, be disposed inside casing. In such an embodiment, the production tubing may provide a conduit for some or all of the production 121 (e.g., oil and gas) passing through the wellbore 120 and the casing.

In some embodiments, the well surface system 124 includes a wellhead 130. The wellhead 130 may include a rigid structure installed at the up-hole end of the wellbore 120, at or near where the wellbore 120 terminates at the surface 108. The wellhead 130 may include structures for supporting (or "hanging") casing and production tubing extending into the wellbore 120. Production 121 may flow through the wellhead 130, after exiting the wellbore 120 and the well sub-surface system 122, including, for example, the casing and the production tubing. In some embodiments, the well surface system 124 includes flow regulating devices that are operable to control the flow of substances into and out of the wellbore 120. For example, the well surface system 124 may include one or more production valves 132 that are operable to control the flow of production 134. A production valve 132 may be fully opened to enable unrestricted flow of production 121 from the wellbore 120. Further, the production valve 132 may be partially opened to partially restrict (or "throttle") the flow of production 121 from the wellbore 120. In addition, the production valve 132 may be fully closed to fully restrict (or "block") the flow of production 121 from the wellbore 120, and through the well surface system 124.

In some embodiments, the wellhead 130 includes a choke assembly. For example, the choke assembly may include hardware with functionality for opening and closing the fluid flow through pipes in the well system 106. Likewise, the choke assembly may include a pipe manifold that may lower the pressure of fluid traversing the wellhead. As such, the choke assembly may include a set of high-pressure valves and at least two chokes. These chokes may be fixed or adjustable or a mix of both. Redundancy may be provided so that if one choke is taken out of service, the flow can be directed through another choke. In some embodiments, pressure valves and chokes are communicatively coupled to the operation system 126. Accordingly, the operation system 126 may obtain wellhead data regarding the choke assembly as well as transmit one or more commands to components within the choke assembly in order to adjust one or more choke assembly parameters.

Keeping with FIG. 1, in some embodiments, the well surface system 124 includes a surface sensing system 134. The surface sensing system 134 may include sensors for sensing characteristics of substances, including production 121, passing through or otherwise located in the well surface system 124. The characteristics may include, for example, pressure, temperature and flow rate of production 121 flowing through the wellhead 130, or other conduits of the well surface system 124, after exiting the wellbore 120. The surface sensing system 134 may also include sensors for sensing characteristics of the rig 101, such as bit depth, hole depth, drilling mudflow, hook load, rotary speed, etc.

In some embodiments, the surface sensing system 134 includes a surface pressure sensor 136 operable to sense the pressure of production 151 flowing through the well surface system 124, after it exits the wellbore 120. The surface pressure sensor 136 may include, for example, a wellhead pressure sensor that senses a pressure of production 121 flowing through or otherwise located in the wellhead 130. In some embodiments, the surface sensing system 134 includes a surface temperature sensor 138 operable to sense the temperature of production 151 flowing through the well surface system 124, after it exits the wellbore 120. The surface temperature sensor 138 may include, for example, a wellhead temperature sensor that senses a temperature of production 121 flowing through or otherwise located in the wellhead 130, referred to as "wellhead temperature" ($T_{wh}$). In some embodiments, the surface sensing system 134 includes a flow rate sensor 139 operable to sense the flow rate of production 151 flowing through the well surface system 124, after it exits the wellbore 120. The flow rate sensor 139 may include hardware that senses a flow rate of production 121 ($Q_{wh}$) passing through the wellhead 130. In some embodiments, downhole sensors and gauges are operable to capture production-related data (e.g., pressures, temperatures, etc.).

While FIG. 1 illustrates a configuration of components, other configurations may be used without departing from the scope of the disclosure. For example, various components in FIG. 1 may be combined to create a single component. As another example, the functionality performed by a single component may be performed by two or more components.

Figure 2:
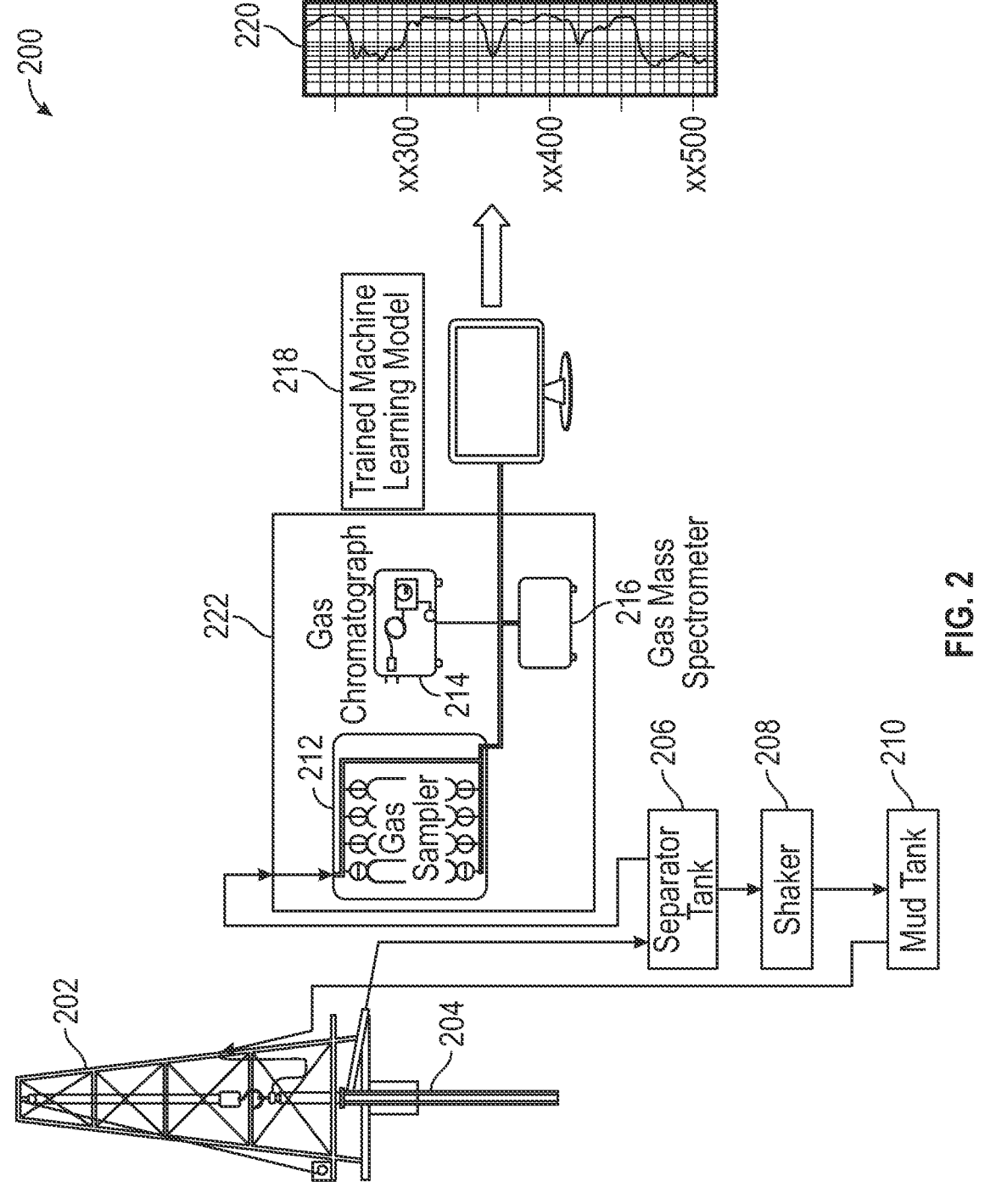
FIG. 2 is a flow diagram that illustrates a method for predicting formation pore pressure based on mud gas data, according to one or more example embodiments.

FIG. 2 is a flow diagram that illustrates a method for predicting formation pore pressure based on mud gas data, according to one or more example embodiments. As shown in FIG. 2, during drilling operation of a well 202, mud is pumped down the wellbore 204 of the well 202 to the formation through the drill pipe of the well 202. The mud lubricates the drill bit during drilling operations, and, when returning to the surface, carries drill cuttings and other debris from the wellbore to the surface. The returned mud is collected at the surface in a separator tank 206 where the mud is degassed using an agitator (not shown). The degassed mud flows over a shale shaker 208 where the mud is filtered away from the cuttings and other debris. The cuttings and other debris are conveyed away for analysis (e.g., by a geologist) while the filtered mud is collected in a mud tank 210 to be pumped back to the wellbore 204.

The gas mixture that is extracted from the mud is conveyed through a vacuum pipeline to an analysis tool (e.g., a logging unit) 222. The analysis tool 222 may include a gas sampler 212, a gas chromatograph 214, and a gas spectrometer 216 that separate and measure the different gas components of the gas mixture. The gas sampler 212 obtains samples from the gas mixture that are used for determination of the chemical composition of the gases in the gas mixture. The gas chromatograph 214 is used to measure the individual light gas components in the gas mixture, such as for example, C1 to C8. The gas spectrometer 216 is used to measure the individual heavy gas components in the gas mixture, such as for example, benzene, toluene, helium, and methylcyclohexane. In some instances, the measurements are made in part per million (ppm) of the respective gas components. The data generated by the gas sampler 212, the gas chromatograph 214, and the gas spectrometer 216 may be referred to as mud gas data and may be used for further analysis associated with the well 202 or other wells.

Using a trained ML model 218 and the mud gas data, a system may estimate pore pressure values associated with various depths of the well 202. In some example embodiments, a ML model, such as an artificial neural network (ANN), a support vector machine, a decision tree, a random forest, a multivariate linear regression, etc., may be trained to determine one or more relationships between mud gas data from a well and corresponding pore pressure data from the well.

According to various example embodiments, the ML model is an ANN model that is trained using supervised machine learning. The ANN model may be configured and optimized with one or more hidden layers (depending on the volume and complexity of the training data), a sigmoid activation function in the hidden layer, a linear function in the summation layer, and training algorithms based on the Levenberg-Marquardt and Bayesian regulation backpropagation. Integrated datasets of mud gas and pore pressure from one or more existing wells may be used to train the ANN model. The ANN model is trained by processing examples. Each example contains a known "input" (e.g., a mud gas value) and "output" (e.g., a pore pressure value). The training includes forming probability-weighted associations between the input and the output, which are stored within the data structure of the neural net. The training of the ANN model from a given example may be conducted by determining the difference between the processed output of the ANN model (i.e., a prediction) and a target output. This difference is an error value. The ANN model then adjusts its weighted associations based on a learning rule and the error value. Successive adjustments may cause the ANN model to produce output which is increasingly similar to the target output. After a number of these adjustments the training may be concluded based upon certain criteria (e.g., the difference between the predicted output and the target output is below a threshold value). Upon completing the training of the ANN model, a mud gas value that is acquired in real time from a new well being drilled and that is associated with a depth of the new well may be used as input into the ANN model to generate an estimated pore pressure value as an output corresponding to the mud gas value associated with the depth of the new well. At any time during the drilling, the output may be analyzed to determine possible cases of under-pressure or over-pressure. As shown in FIG. 2, the estimate pore pressure value may be included in a pore pressure value log 220.

Figure 3:
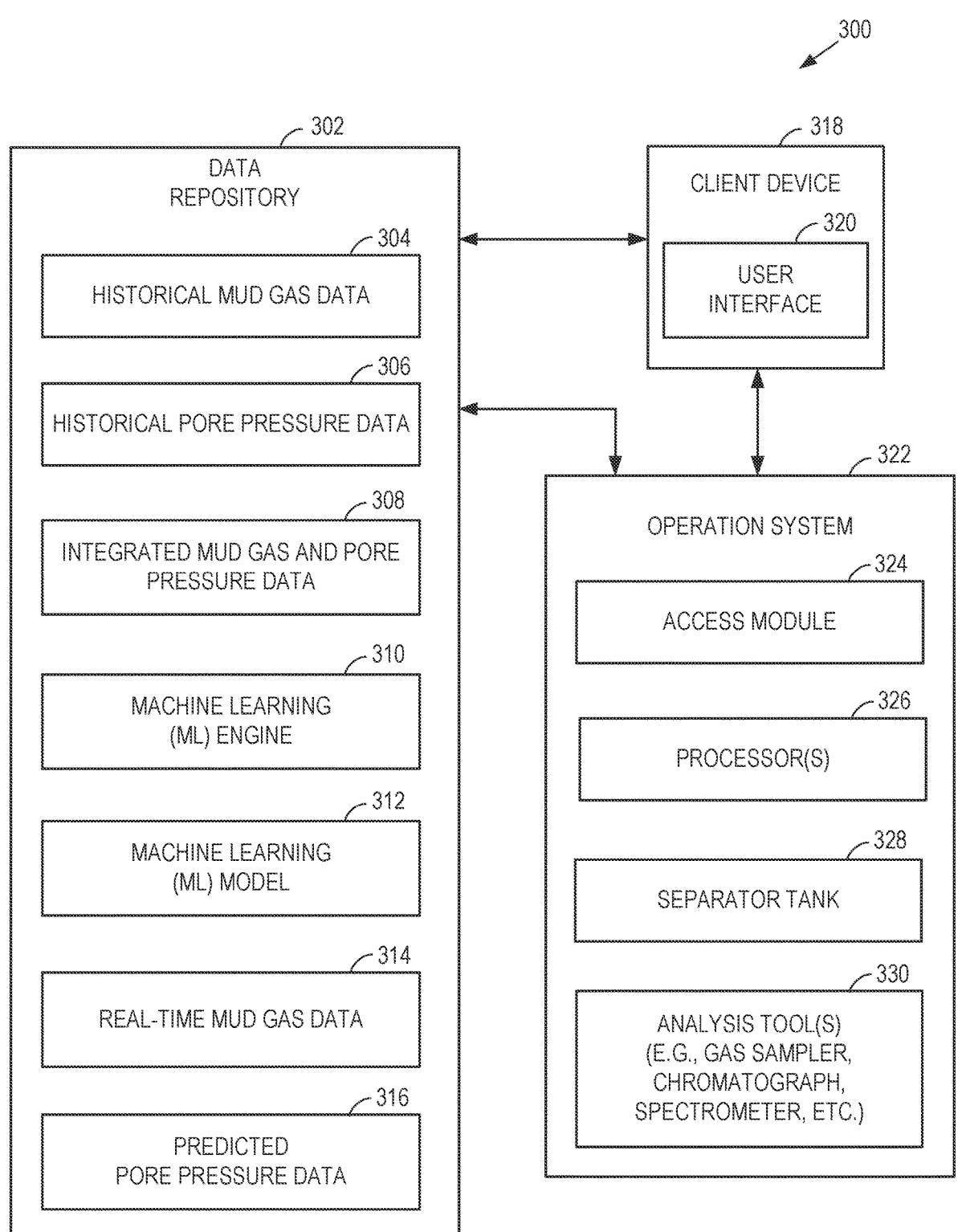
FIG. 3 is a block diagram that illustrates a system for estimating a pore pressure value based on mud gas data, according to one or more example embodiments.

FIG. 3 is a block diagram that illustrates a system 300 for estimating a pore pressure value based on mud gas data, according to one or more example embodiments. System 300 includes an operation system 322, a data repository 302, and a client device 318.

The components of the operation system 322 are operatively connected and are configured to communicate with each other (e.g., via a bus, shared memory, a switch, wirelessly, etc.). In addition, the operation system 322 is configured to communicate with the data repository 302 to access and store data. Also, the operation system 322 is configured to communicate with the client device 318.

The operation system 322 is shown as including an access module 324, one or more processors 326, a separator tank 328 that may include an agitator, and one or more analysis tools 330. The separator tank 328 collects the mud that is returned to the surface. Using the agitator, the separator tank 328 degasses a gas mixture from the received mud (e.g., separates one or more mud gasses from the liquid and solid components of the returned mud). The gas mixture is used for determination of the chemical composition of the gases in the gas mixture.

The one or more analysis tools 330 may include a gas sampler, a gas chromatograph and a gas spectrometer. The gas sampler obtains samples from the gas mixture. The gas chromatograph measures the individual light gas components in the gas rnixture. The gas spectrometer measures the individual heavy gas components in the gas mixture. The data generated by the one or more analysis tools 330 (e.g., the gas sampler, the gas chromatograph, or the gas spectrometer) may be referred to as mud gas data.

The data repository 302 may store historical mud gas data 304 obtained based on the analysis of mud gases from existing wells. In addition, the data repository 302 may store historical pore pressure data 306 obtained from the existing wells. The historical pore pressure data 306 may correspond to the historical mud gas data 304. For example, a particular pore pressure value may be associated with a particular depth of an existing well. In addition, certain mud gas data (e.g., a mud gas value) may be associated with the particular depth of the existing well. As such, the particular pore pressure value may correspond to the certain mud gas data.

Further, the data repository 302 may store integrated mud gas and pore pressure data 308 associated with one or more existing wells. In some example embodiments, the integrated mud gas and pore pressure data 308 is generated based on integrating the historical mud gas data 304 associated with the one or more existing wells and corresponding historical pore pressure data 306 associated with the one or more existing wells. The corresponding historical pore pressure data 306 corresponds to the historical mud gas data 304 based on one or more depth values that identify one or more depths of the one or more existing wells and based on one or more time values. In some instances, a particular time value of the one or more time values is a timestamp identifying the time when a particular historical mud gas value included in the historical mud gas data 304 and a particular corresponding historical pore pressure value included in the corresponding historical pore pressure data 306 were obtained.

The data repository 302 may also store an ML engine 310 that may be used, by the one or more hardware processors 324, to train a ML model. Further, the data repository 302 may store mud gas data obtained in real-time (or near real-time) during the drilling operations of a new well. Such data may be stored as real-time mud gas data 314 in the data repository 302.

The access module 324 is configured to access the integrated mud gas and pore pressure data 308 and the ML engine 310 from the data repository 302. The access module 324 is further configured to access the real-time mud gas data 314 associated with a depth value that identifies the depth of a well subject to the drilling operations.

The one or more hardware processors 326 are configured to train an ML model 312 using the ML engine 310 and the integrated mud gas and pore pressure data 308. The trained ML model 312 may be stored in the data repository 302.

The one or more hardware processors 326 are further configured to estimate, during the drilling operations of a new well, a pore pressure value of a formation zone, at the depth of the new well, using the trained ML model 312 and the real-time mud gas data 314 associated with the depth value that identifies the depth of the new well subject to the drilling operations. The estimated pore pressure value may be stored as predicted pore pressure data 316 in the data repository 302.

The one or more hardware processors 326 are also configured to update a drilling program for a production system based on the estimated pore pressure value. The drilling program may be executed on a computing device such as that shown in FIG. 7. In some example embodiments, the updating of the drilling program for the production system includes generating, by the one or more hardware processors 326, of a workorder based on the estimated pore pressure value. The one or more hardware processors 326 may also cause display of the workorder in a user interface 320 of the client device 318.

The operation system 322 is also configured to communicate with the client device 318 that includes the user interface 320. The client device 216 may include a computing device that includes at least a display and communication capabilities to communicate with the operation system 322, the data repository 302, and the production system via an electronic network. The client device 318 may comprise, but is not limited to, a computer, a work station, a desktop, a laptop, a tablet, a smart phone, a hand-held device, an Internet appliance, a wearable device, a smart phone, a cellular (or mobile) phone, a multi-processor system, a mini-computer, etc. The user interface 320 may be a graphical user interface (GUI) or a command line interface. The user interface 320 may display data retrieved, accessed, or received from the data repository 302, the operation system 322, and the production system on a display device, such as a computer monitor or a touchscreen on the client device 318. Furthermore, the user interface 320 may present data to a user, for example, through text or rendered by the client device 318 into a visual representation of the data, such as through visualizing a data model.

In some example embodiments, the operation system 322 generates a communication that references the estimated pore pressure value and provides a recommendation of an action with respect to the estimated pore pressure value. The operation system 322 transmits the communication to the client device 318 and causes display of the communication in the user interface 320 of the client device 318.

In some example embodiments, the user of the client device 318 accesses the operation system 322 via the user interface 320. The client device 318 is also configured to communicate with the data repository 302 to access and store data. In addition, the client device 318 is also config-ured to communicate with the production system.

FIG. 4 is a flow diagram that illustrates an algorithm for training a machine learning model to predict pore pressure values based on mud gas data, according to one or more example embodiments. The operation system 322 trains a ML model to estimate a pore pressure value of a formation, at a depth of a new well that is undergoing drilling opera-tions, based on corresponding mud gas data associated with the depth of the new well. The ML model is trained using a ML engine, historical mud gas data from one or more existing wells, and corresponding historical pore pressure values from the one or more existing wells. Steps of the algorithm 400 may be performed using the components described above with respect to FIG. 3. One or more blocks in FIG. 4 may be performed by a computing system such as that shown and described below in FIG. 7.

At Step 402, a processor 326 generates an integrated dataset for training and validating the ML model based on the historical mud gas data 304 and corresponding historical pore pressure data 306. A historical pore pressure value corresponds to a historical mud gas value when both the historical pore pressure value and the historical mud gas value are associated with the same well and the same depth of the well.

At Step 404, the processor 326 generates a calibration dataset and a validation dataset based on the integrated dataset. For example, the processor 326 divides the inte-grated dataset into a calibration dataset and a validation dataset.

At Step 406, the processor 326 trains the ML model to predict a pore pressure value at a depth of a well. The training of the ML model is performed using the calibration dataset.

At Step 408, the access module 324 accesses an actual (e.g., a target) pore pressure value associated with the depth of the well, from the validation dataset.

At Step 410, the processor 326 determines whether the error between the predicted pore pressure value and the actual pore pressure value is less or equal to an error threshold value.

If the error is determined to be greater than the error threshold value, the processor 326, at Step 412, adjusts one or more learning parameters of the ML model, and the processor 326 repeats Step 406 based on the one or more adjusted learning parameters.

However, if the error is determined to be less or equal to the error threshold value, the processor 326, at Step 414, identifies the trained ML model as a validated model.

At Step 416, the processor 326 predicts one or more pore pressure values for one or more depths of a new well during the drilling operations of the new well. The prediction of the one or more pressure values is performed based on the validated ML model and the input of real-time mud gas data associated with the one or more depths of the new well.

FIG. 5 is a flowchart illustrating operations of a system 318 in performing a method 500 for training the ML model to estimate a pore pressure value based on mud gas data, according to one or more example embodiments. Steps of the method 500 may be performed using the components described above with respect to FIG. 3. One or more blocks in FIG. 5 may be performed by a computing system described below with respect to FIG. 7. While the various blocks in FIG. 5 are presented and described sequentially, one of ordinary skill in the art will appreciate that some or all of the blocks may be executed in different orders, may be combined or omitted, and some or all of the blocks may be executed in parallel. Furthermore, the blocks may be per-formed actively or passively.

At Step 502, an access module 324 accesses mud gas data associated with an existing well (e.g., the historical mud gas data 304). The access module 324 may access the mud gas data from the data repository 302.

At Step 504, the access module 324 accesses pore pres-sure data associated with the existing well and correspond-ing to the mud gas data (e.g., the historical pore pressure data 306). The access module 324 may access the pore pressure data from the data repository 302. In some example embodi-ments, the pore pressure data corresponds to the mud gas data based on one or more depth values of the existing well.

In some instances, the processor 326 integrates the mud gas data associated with the existing wells and the pore pressure data associated with the existing wells. In some example embodiments, integration is performed via hori-zontal concatenation, by matching the mud gas data corre-sponding to a certain depth to the pore pressure of the same well corresponding to the same depth. For example, an integrated mud gas and pore pressure data record may indicate that, at depth X100 in well A, when methane (C1) was X1, ethane (C2) was X2, propane (C3) was X3, etc., the pore pressure was Y, where X100 identifies a depth value of the well A, X1, X2, and X3 identify volume values of C1, C2, and C3, respectively, and Y identifies a pore pressure value at depth X100.

In addition, the processor 326 may generate a training (e.g., a calibration) dataset for training the ML model. The generating of the training dataset may be based on the integrated mud gas data associated with the existing wells and the pore pressure data associated with the existing wells. Further, the processor 326 may generate a validation dataset for validating (or optimizing) the trained ML model. The generating of the validation dataset may be based on the integrated mud gas data associated with the existing wells and the pore pressure data associated with the existing wells.

At Step 506, the processor 326 trains the ML model to determine one or more relationships between the mud gas data and the pore pressure data, and to output (or generate) an estimated pore pressure value of a formation zone, at the depth of a well subject to the drilling operations. The outputting (or generating) of the estimated pore pressure value is based on the one or more relationships between the mud gas data and the pore pressure data, and on mud gas data associated with the well subject to the drilling opera-tions.

In various example embodiments, the mud gas data includes a mud gas log and the pore pressure data includes a pore pressure log. The determining of one or more rela-tionships between the mud gas data and the pore pressure data includes generating a nonlinear mathematical relation-ship between the mud gas log and the pore pressure log based on multiplying the mud gas log by a weight factor value. The weight factor value is determined based on a nonlinear degree of correlation between the mud gas log and the pore pressure log. The outputting of the estimated pore pressure value may include generating an output space of the ML model based on applying a function to an input space of the ML model. The input space may include a product of the weight factor and a mud gas value included in the mud gas log. The output space may include one or more estimated pore pressure values including the estimated pore pressure value.

In various example embodiments, the processor 326 determines whether the trained ML model may be identified as a validated model or whether further training of the ML model should be performed, for example, by performing adjustments of one or more learning parameters. For example, the processor 326 determines that a difference between the estimated pore pressure value that is output by the ML model and an actual pore pressure value that is included in a validation dataset exceeds an error threshold value. The processor 326 adjusts a learning parameter of the ML model to a pre-determined value based on the determination that the difference between the estimated pore pressure value output by the ML model and the actual pore pressure value included in the validation dataset exceeds the error threshold value.

According to a different example, the processor 326 determines that a difference between the estimated pore pressure value that is output by the ML model and an actual pore pressure value that is included in a validation dataset does not exceed an error threshold value. The processor 326 identifies the ML model as being validated for receiving real-time mud gas data associated with a new well, as input to estimate a pore pressure log for the new well during drilling operations of the new well.

In some example embodiments, the access module 324 accesses mud gas data associated with the drilling operations of a new well. The access module 324 accesses pore pressure data associated with the new well and corresponding to the mud gas data associated with the drilling operations of the new well. The processor 326 calibrates the trained ML model based on the mud gas data associated with the drilling operations of the new well and the pore pressure data associated with the new well.

FIG. 6 is a flowchart illustrating operations of a system 318 in performing a method 600 for estimating a pore pressure value based on mud gas data during drilling operations, according to one or more example embodiments. Steps of the method 600 may be performed using the components described above with respect to FIG. 3. One or more blocks in FIG. 6 may be performed by a computing system described below with respect to FIG. 7. While the various blocks in FIG. 6 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

At Step 602, an access module 324 accesses mud gas data associated with a depth value that identifies the depth of a well subject to the drilling operations. In some example embodiments, the mud gas data is generated based on analysis, by the analysis tool 330, of a gas mixture degassed from the mud returned to the surface during the drilling operations of the well. In various example embodiments, the mud gas data includes data pertaining to one or more light gases that are liberated from the formation zone during the drilling operations. In certain example embodiments, the mud gas data includes data pertaining to one or more heavy gases that are liberated from the formation zone during the drilling operations.

At Step 604, the processor 326 generates an estimated pore pressure value of a formation zone, at the depth of the well, during the drilling operations. The generating is performed using the mud gas data and a trained machine learning model.

At Step 606, the processor 326 updates a drilling program for a production system based on the estimated pore pressure value. In some example embodiments, the updating of the drilling program includes determining that the estimated pore pressure value deviates from a hydrostatic pressure value of the well by at least a threshold value and determining a cause of the deviation. There is a certain hydrostatic pressure threshold range that defines a window for safe hydrostatic pressure. The condition when the pore pressure value is below the hydrostatic pressure threshold range is called underpressure. In some instances, underpessure may be caused by the existence of a fractures, faults, or vugs. The condition when the pore pressure value is above the hydrostatic pressure threshold range is called overpressure. In some instances, overpressure is caused by an influx of formation gas (gas kick). The latter condition may lead to a dangerous event such as blowout, while the former condition may cause lost circulation of the mud (i.e., the mud pumped into the wellbore is not retrieved at the surface).

Figure 7:
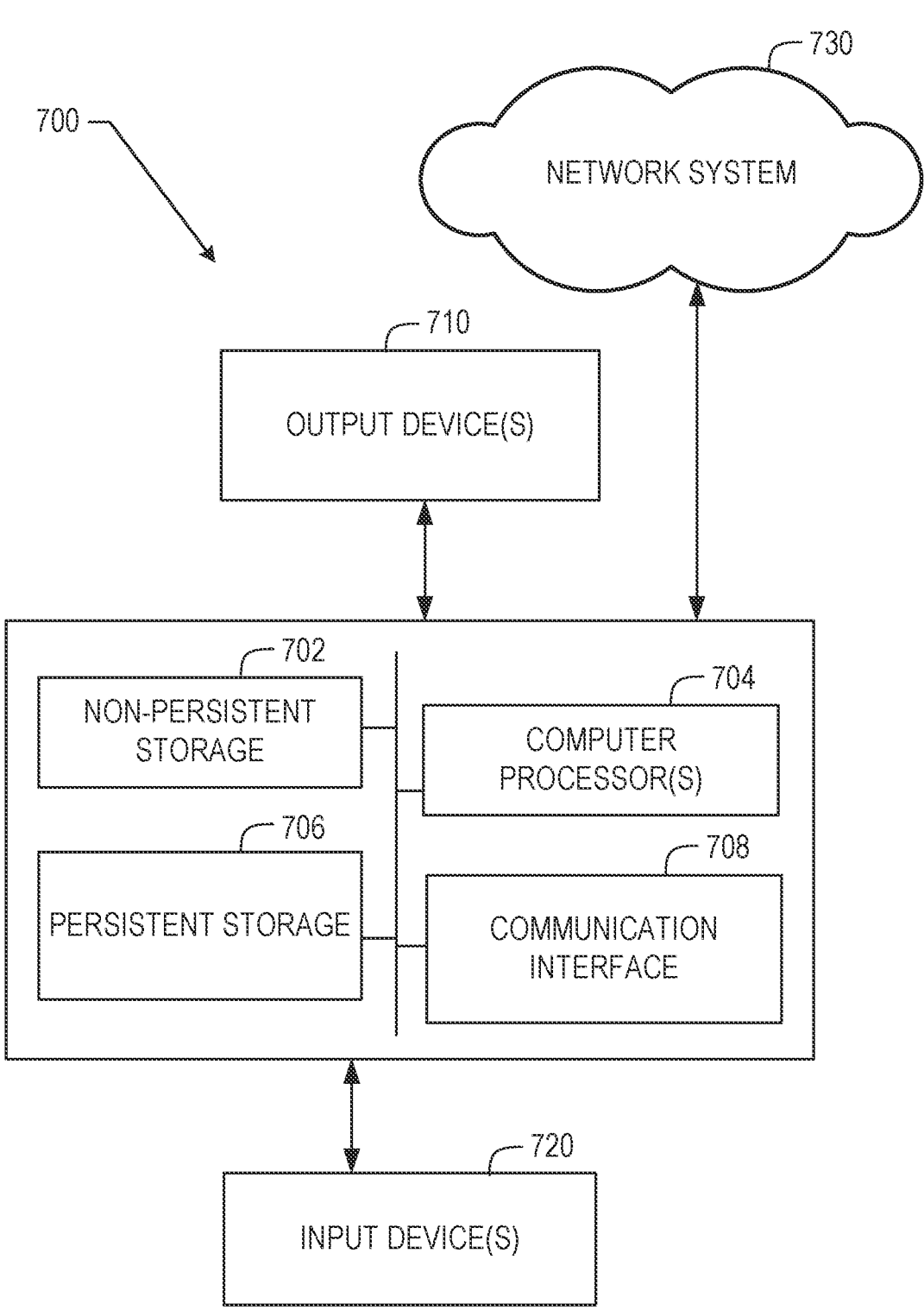
FIG. 7 illustrates a computing system, according to one or more example embodiments.

Turning to FIG. 7, FIG. 7 shows a computing system in accordance with one or more embodiments. As shown in FIG. 7, the computing system 700 may include one or more computer processor(s) 704, non-persistent storage 702 (e.g., random access memory (RAM), cache memory, or flash memory), persistent storage 706 (e.g., a hard disk), a communication interface 708 (e.g., transmitters and/or receivers), as well as other elements. The computer processor(s) 704 may be an integrated circuit for processing instructions. The computing system 700 may also include one or more input device(s) 720, such as a touchscreen, a keyboard, a mouse, a microphone, a touchpad, an electronic pen, or any other type of input device. In some embodiments, the one or more input device(s) 720 may be a graphical user interface (GUI). Further, the computing system 700 may include one or more output device(s) 710, such as a screen (e.g., a liquid crystal display (LCD), a plasma display, or a touchscreen), a printer, external storage, or any other output device. One or more of the output device(s) 710 may be the same or different from the input device(s) 720. The computing system 700 may be connected to a network system 730 (e.g., a local area network (LAN), a wide area network (WAN) such as the Internet, a mobile network, or any other type of network) via a network interface connection.

In one or more embodiments, for example, the input device 720 may be coupled to a receiver and a transmitter used for exchanging communications with one or more peripherals connected to the network system 730. The transmitter may relay information received by the receiver to other elements of the computing system 700. Further, the computer processor(s) 704 may be configured for performing or aiding in implementing the processes described in reference to FIGS. 1-6.

Further, one or more elements of the computing system 700 may be located at a remote location and may be connected to the other elements over the network system 730. The network system 730 may be a cloud-based interface that performs processing at a remote location, away from the well site, and that is connected to the other elements over a network. In this case, the computing system 700 may be connected through a remote connection established using a 5G connection, such as protocols established in Release 15 and subsequent releases of the 3GPP/New Radio (NR) standards.

The computing system of FIG. 7 may include or may be connected to a data repository. The data repository may be a database. A database is a collection of information configured for ease of data retrieval, modification, re-organization, and deletion. In some embodiments, the database includes measured data relating to the methods, the systems, and the devices as described in reference to FIGS. 1-6.

While FIGS. 1-9 show various configurations of components, other configurations may be used without departing from the scope of the disclosure. For example, various components may be combined to create a single component. As another example, the functionality performed by a single component may be performed by two or more components.

Although only a few example embodiments have been described in detail above, those skilled in the art will readily appreciate that many modifications are possible in the example embodiments without materially departing from this description. Accordingly, all such modifications are intended to be included within the scope of this disclosure as defined in the following claims. In the claims, means-plus-function clauses are intended to cover the structures described herein as performing the recited function and not only structural equivalents, but also equivalent structures. It is the express intention of the applicant not to invoke 35 U.S.C. § 112(f) for any limitations of any of the claims herein, except for those in which the claim expressly uses the words "means for" together with an associated function.

What is claimed:

1. A system for estimating a pore pressure value associated with a depth of a new well subject to drilling operations, the system comprising:

a data repository for storing integrated mud gas and pore pressure data associated with one or more existing wells, and a machine learning (NIL) engine, wherein the integrated mud gas and pore pressure data is generated by integrating historical mud gas data with historical pore pressure data according to a correspondence comprising:

one or more depth values that identify one or more depths of the one or more existing wells; and a nonlinear mathematical relationship determined by multiplying the historical mud gas data by a weight factor value, wherein the weight factor value is determined by a nonlinear degree of correlation between the historical mud gas data and the historical pore pressure data, thereby forming a depth-specific predictive relationship for an estimation of pore pressure;

an access module configured to:

access the integrated mud gas and pore pressure data, access the ML engine, and access real time mud gas data comprising a real time mud gas value and an associated depth value that identifies the depth of the new; and one or more hardware processors configured to:

train a ML model using the ML engine and the integrated mud gas and pore pressure data, wherein the trained ML model is configured to receive the real time mud gas data associated with the depth of the new well and generate the estimated pore pressure value of a formation zone of the new well based on the real time mud gas data; and during the drilling operations, iteratively:

obtain, via the access module, the real time mud gas data;

input the real time mud gas data into the trained ML model to obtain the estimated pore pressure value corresponding to the real time mud gas value and the associated depth value; and update a drilling program for a production system of the new well using the estimated pore pressure value, wherein updating the drilling program comprises adjusting a density of drilling mud weight at a drill bit to stabilize a hydrostatic pressure of the new well and mitigate a risk of underpressure or overpressure.

2. The system of claim 1, the system further comprising:

a separator tank configured to:

collect returned mud that is returned to a surface during the drilling operations of the new well, and degas a gas mixture from the returned mud; and an analysis tool configured to generate the real time mud gas data based on analysis of the gas mixture.

3. The system of claim 1, wherein the real time mud gas data includes data pertaining to a light gas that is liberated from the formation zone during the drilling operations.

4. The system of claim 1, wherein the real time mud gas data includes data pertaining to a heavy gas that is liberated from the formation zone during the drilling operations.

5. The system of claim 1, wherein during the updating of the drilling program, the one or more hardware processors is further configured to:

determine that the estimated pore pressure value deviates from a hydrostatic pressure value of the new well by at least a threshold value; and determine a cause of the deviation.

6. A method for estimating a pore pressure value associated with a depth of a new well during drilling operations, the method comprising:

during the drilling operations, iteratively:

accessing real time mud gas data comprising a real time mud gas value and an associated depth value that identifies the depth of the new well;

generating an estimated pore pressure value of a formation zone at the depth of the new well using one or more hardware processors and a trained machine learning (ML) model, wherein the trained ML model is configured to receive the real time mud gas data associated with the depth of the new well and generate the estimated pore pressure value of a formation zone of the new well based on the real time mud gas data;

wherein the ML model is trained using integrated mud gas and pore pressure data associated with one or more existing wells, wherein the integrated mud gas and pore pressure data is generated by integrating historical mud gas data with historical pore pressure data according to a correspondence comprising:

one or more depth values that identify one or more depths of the one or more existing wells; and a nonlinear mathematical relationship determined by multiplying the historical mud gas data by a weight factor value, wherein the weight factor value is determined by a nonlinear degree of correlation between the historical mud gas data and the historical pore pressure data, thereby forming a depth-specific predictive relationship for an estimation of pore pressure; and updating a drilling program for a production system of the new well using the estimated pore pressure value, wherein updating the drilling program comprises adjusting a density of drilling mud weight at a drill bit to stabilize a hydrostatic pressure of the new well and mitigate a risk of underpressure or overpressure.

7. The method of claim 6, further comprising:

collecting returned mud that is returned to a surface during the drilling operations of the new well;

degassing a gas mixture from the returned mud; and generating the real time mud gas data based on analysis of the gas mixture.

8. The method of claim 6, wherein the real time mud gas data includes data pertaining to a light gas that is liberated from the formation zone during the drilling operations.

9. The method of claim 6, wherein the real time mud gas data includes data pertaining to a heavy gas that is liberated from the formation zone during the drilling operations.

10. The method of claim 6, wherein the updating of the drilling program includes:

determining that the estimated pore pressure value deviates from a hydrostatic pressure value of the new well by at least a threshold value; and determining a cause of the deviation.

11. A method for training a machine learning (ML) model to estimate a pore pressure value associated with a depth of a new well subject to drilling operations, the method comprising:

accessing a mud gas log associated with an existing well, wherein the mud gas log comprises historical mud gas data;

accessing a pore pressure log associated with the existing well and corresponding to the mud gas log, wherein the pore pressure log comprises historical pore pressure data; and training, using one or more hardware processors, the ML model to:

receive real time mud gas data associated with the depth of the new well and generate an estimated pore pressure value of a formation zone of the new well based on the real time mud gas data, wherein the ML model is trained using an integrated dataset comprising the historical mud gas data and the historical pore pressure data to determine one or more relationships between mud gas characteristics and pore pressure, wherein the integrated dataset is generated by integrating the historical mud gas data with the historical pore pressure data according to a correspondence comprising:

one or more depth values that identify one or more depths of the existing well; and a nonlinear mathematical relationship generated by multiplying the historical mud gas data by a weight factor value, wherein the weight factor value is determined by a nonlinear degree of correlation between the historical mud gas data and the historical pore pressure data, thereby forming a depth-specific predictive relationship for an estimation of pore pressure;

wherein, during the drilling operations, the one or more hardware processors is configured to iteratively:

obtain the real time mud gas data comprising a real time mud gas value and an associated depth value that identifies the depth of the new well;

input the real time mud gas data into the trained ML model to obtain the estimated pore pressure value corresponding to the real time mud gas value and the associated depth value; and update a drilling program for a production system of the new well using the estimated pore pressure value, wherein updating the drilling program comprises adjusting a density of drilling mud weight at a drill bit to stabilize a hydrostatic pressure of the new well and mitigate a risk of underpressure or overpressure.

12. The method of claim 11, wherein the outputting of the estimated pore pressure value includes:

generating an output space of the ML model based on applying a function to an input space of the ML model, the input space including a product of the weight factor and a mud gas value included in the mud gas log, the output space including one or more estimated pore pressure values including the estimated pore pressure value.

13. The method of claim 11, further comprising:

determining that a difference between the estimated pore pressure value that is output by the ML model and an actual pore pressure value that is included in a validation dataset exceeds an error threshold value; and adjusting a learning parameter of the ML model to a pre-determined value.

14. The method of claim 11, further comprising:

determining that a difference between the estimated pore pressure value that is output by the ML model and an actual pore pressure value that is included in a validation dataset does not exceed an error threshold value; and identifying the ML model as being validated for receiving the real time mud gas data associated with the new well, as input to estimate a real time pore pressure log for the new well during the drilling operations of the new well.

15. The method of claim 11, further comprising:

accessing the real time mud gas data associated with the drilling operations of the new well;

accessing real time pore pressure data associated with the new well and corresponding to the real time mud gas data associated with the drilling operations of the new well; and calibrating the trained ML model based on the real time mud gas data associated with the drilling operations of the new well and the real time pore pressure data associated with the new well.

16. The method of claim 11, wherein the real time mud gas data includes data pertaining to a light gas that is liberated from the formation zone during the drilling operations.

17. The method of claim 11, wherein the real time mud gas data includes data pertaining to a heavy gas that is liberated from the formation zone during the drilling operations.

* * * * *